| United States Patent [19] | [11] Patent Number: 4,748,115 |
| --- | --- |
| Steaffens | [45] Date of Patent: May 31, 1988 |

[54] SUBSTRATE FORMULATION IN 2-AMINO-2-METHYL-1-PROPANOL BUFFER FOR ALKALINE PHOSPHATASE ASSAYS

[75] Inventor: Jeffrey W. Steaffens, Gurnee, Ill.

[73] Assignee: Abbott Laboratories, North Chicago, Ill.

[21] Appl. No.: 817,090

[22] Filed: Jan. 8, 1986

[51] Int. Cl.$^4$ ............ C12Q 1/42; G01N 33/535
[52] U.S. Cl. .......................... 435/21; 435/4; 435/7; 435/188; 436/805
[58] Field of Search .............. 435/4, 7, 21, 188; 436/805

[56] References Cited

U.S. PATENT DOCUMENTS 4,030,995  6/1977  Starkweather ............ 435/814
4,563,417  1/1986  Albarella et al. ............ 435/7

OTHER PUBLICATIONS

Leary, Jeffrey J. et al., "Rapid and Sensitive Colorimetric Method for Visualizing Biotin–labeled DNA probes hydridized to DNA or RNA immobilized on nitrocellalose:Bio blots", PNAS (80), pp. 4045–4049, Jul. 1983.

*Primary Examiner*—Sidney Marantz
*Assistant Examiner*—Janelle Graeter
*Attorney, Agent, or Firm*—Martin L. Katz

[57] ABSTRACT

A stable substrate formulation for an alkaline phosphatase assay includes 5-bromo-4-chloro-3-indolyl phosphate, nitro blue tetrazolium and a 2-amino-2-methyl-1-propanol buffer. Addition of $MgCl_2$ to this formulation promotes stability.

10 Claims, 3 Drawing Sheets

SUBSTRATE FORMULATION IN 2-AMINO-2-METHYL-1-PROPANOL BUFFER FOR ALKALINE PHOSPHATASE ASSAYS

BACKGROUND

The present invention pertains in general to substrate formulations for enzyme assays, and, in particular, to substrate formulations for alkaline phosphatase assays which include a phosphated indigo cogener and a tetrazolium salt.

Assays for the detection of substances present in small amounts rely upon the use of indicators. In biological assays, one type of indicator involves the use of an enzyme attached to a probe which preferentially binds to a target substance to be detected. Once bound to the target, the enzyme may function as a reporter group by catalyzing a reaction with a substrate to produce a product which is readily detectable by unaided vision or by a machine.

One example of an enzyme which is capable of serving as a reporter group is alkaline phosphatase. The term alkaline phosphatase generally refers to a group of non-specific enzymes which hydrolyze monophosphoric esters over a pH range of approximately 8.5 to 10.5.

Although a number of substrates may be reacted with an alkaline phosphatase enzyme, reaction with an indigo cogener, preferably a 3-indolyl phophate salt such as 5-bromo-4-chloro-3-indolyl phosphate (BCIP), produces a particularly useful signal. Alkaline phosphatase degrades BCIP into an organic moiety and a phosphate. The organic moieties dimerize to form a blue-colored product. A transphosphorylating buffer removes the phosphate transferred from the indigo cogener by the enzyme, thus avoiding accumulation of phosphate by the enzyme and consequent enzyme inhibition. Transphosphorylating buffers useful in such reactions include 2-amino-2-methyl-1-propanol (2A2M1P), diethanolamine, ethane amino ethanol, and 2-amino-2-methyl-1,3-propandiol. See Starkweather, U.S. Pat. No. 4,030,995; and U. K. Patent No. 1,263,202.

Enhancement of the alkaline phosphatase reaction with BCIP may be achieved by the addition of nitro blue tetrazolium (NBT). The products of the reaction of alkaline phosphatase with BCIP reduce NBT to insoluble blue diformazan, which may produce a stronger signal than is produced by the BCIP reaction products alone. See, e.g., Parent et al., *Phytoprotection*, 66, 53–57 (1985). However, a precipitate forms in an aqueous substrate formulation containing BCIP and NBT with about 24 hours of preparation. Formation of this precipitate is associated with a loss of activity, necessitating the separate packaging of NBT, BCIP and buffer in kits for the preparation of alkaline phosphatase subtrate formulations.

SUMMARY OF THE INVENTION

The present invention provides a stable substrate formulation for an alkaline phosphatase assay. This formulation is sufficiently stable so that NBT, BCIP and buffer may be premixed and packaged as a unit. The formulation includes a phosphated indole cogener, a tetrazolium salt at a concentration effective to produce a detectable signal upon reaction with the phosphated indole cogener, and 2-amino-2-methyl-1-propanol at a concentration effective to buffer a reaction between the phosphated indole cogener and the tetrazolium salt in aqueous solution within a range of pH which allows the reaction to proceed.

It is presently preferred that the substrate formulation according to the present invention include 5-bromo-4-chloro-3-indolyl phosphate at a concentration between about 1.0 mM and about 10 mM., nitro blue tetrazolium at a concentration between about 0.05 mM and about 0.5 mM, and 2-amino-2-methyl-1-propanol at a concentration between about 1.0 M and about 1.0 M. The substrate formulation may also include $MgCl_2$ at a concentration of about 1.0 mM.

It is especially preferred that the substrate formulation according to the present invention include 5-bromo-4-chloro-3-indolyl phosphate at a concentration of 1.2 mM, nitro blue tetrazolium at a concentration of 0.17 mM, 2-amino-2-methyl-1-propanol at a concentration of 100 mM, $MgCl_2$ at a concentration of 1 mM and sodium azide at a concentration of 0.02%.

DETAILED DESCRIPTION

Figure 1:
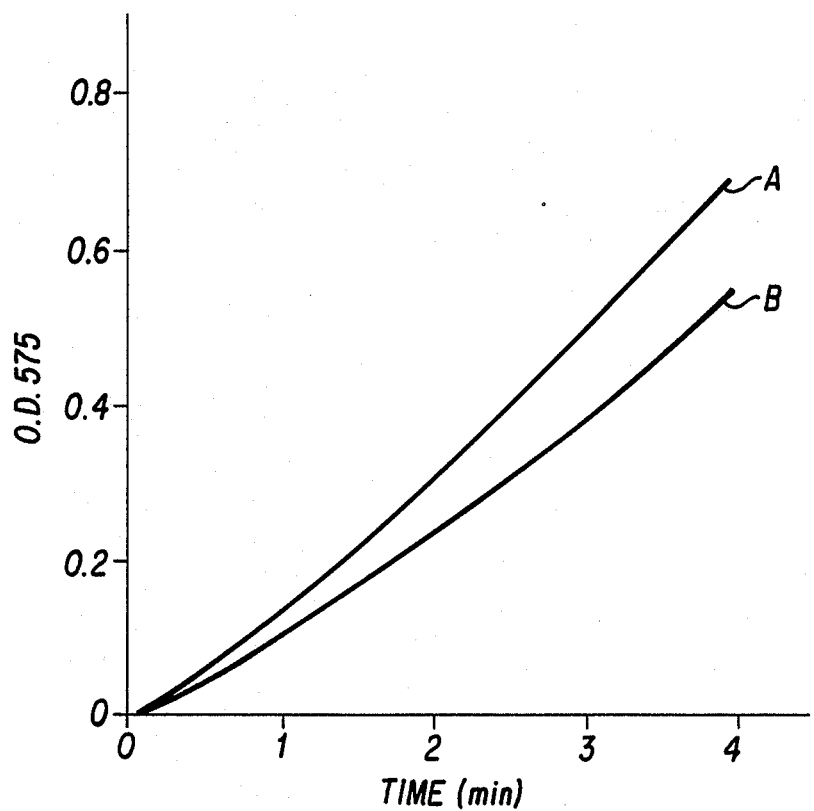
FIG. 1 is a graphic depiction of the rate of substrate color formation in an alkaline phosphatase assay as conducted either in 2A2M1P buffer or in Tris buffer.

Although 2A2M1P is useful for alkaline phosphatase assays performed in the absence of NBT (Starkweather, supra) and is useful for the storage of alkaline phosphatase itself [McComb, et al, in Alkaline Phosphatase, Plenum Press, New York, at 7.5.7.3 (1979)], prior to the present invention it is believed that no special benefit was known to derive from the use of 2A2M1P in alkaline phosphatase substrate formulations containing NBT. As a result, a 2-amino-2(hydroxymethyl)-1,3-propanediol (Tris) buffer is generally employed as a buffer in such formulations despite the consequent inconvenience, expense and potential inaccuracy resulting the need to separately package components of the substrate formulation in order to avoid formation of a precipitate.

In Example 1, substrate formulations are tested to locate the cause of the formation of the precipitate. In Example 2, modified forms of Tris buffer are examined for precipitate formation. In Example 3, organic solvents are added to Tris-buffered substrate formulations in an attempt to inhibit the formation of the precipitate. In Example 4, a number of buffers are unsuccessfully considered as alternatives to Tris, and 2A2M1P is identified as a buffer uniquely suited for stabilizing substrate formulations in alkaline phosphatase assays. In Example 5, color formation in the BCIP/NBT assay is compared for a 2A2M1P-buffered formulation and for a Tris-buffered formulation. In Example 6, concentrations of BCIP and NBT are considered for their effect on signal strength and stability in 2A2M1P. In Example 7, various substrate preparations are examined for long-term stability in 2A2M1P. In Example 8, optimum conditions of use for the 2A2M1P buffer are explored. In Example 9, the stability of a preferred substrate solution of Example 8 is tested. In Example 10, a spectrophotometric comparison of the product of the 2A2M1P-buffered substrate with the product of the Tris-buffered substrate is made. In Example 11, the present invention is examined for use in a solid phase assay. In Example 12, the present invention is examined for use in an enzyme-linked immunosorbent assay (ELISA). In Example 13, The present invention is examined for use in a Western Blot assay.

EXAMPLE 1

In order to determine the cause of the precipitation, solutions were prepared in 0.1 M diethanolamine (pH 9.8) which contained: 1.4 mM BCIP without NBT; 0.24 mN NBT without BCIP; or 1.4 mM BCIP and 0.24 mM NBT. These solutions were observed for the formation of precipitate at room temperature.

No precipitation was observed in the solution containing 1.4 mM BCIP without NBT.

A heavy, blue precipitate was noted in the solution containing 0.24 mM NBT in the absence of BCIP.

A heavy, blue precipitate was also noted in the solution containing both 1.4 mM BCIP and 0.24 mM NBT.

Therefore, it was concluded that the presence of NBT led to the formation of the undesirable precipitate.

EXAMPLE 2

In order to determine whether a modified form of Tris buffer might perform satisfactorily in the BCIP/NBT assay and yet not be prone to formation of a precipitate during storage, the following experiments were performed.

Assays of substrate formulations were performed by mixing enzyme conjugate and substrate in a test tube in order to isolate the substrate formulation from variables which may be introduced by other components of standard assays.

In a test tube assay, 20 μ of conjugate [1:1000 dilution of anti-human antibody conjugated to alkaline phosphatase as supplied at 0.5 mg/ml by Kirkegaard & Perry Laboratories, Inc., Gaithersburg, Md.] were mixed with 1.0 ml of substrate in a cuvette and color development was monitored at a wavelength of 575 nm. A quantitative comparison of reaction rates may be made by calculating the increase in adsorption per minute (ΔA/min) from the following equation.

$$\Delta A/\min = \frac{(A \text{ at } X \min) - (A \text{ at } 2 \min)}{(X - 2)} \quad (1)$$

wherein A is absorption at 575 nm and X is the time point at which a sample is taken.

An initial formulaton of Tris-buffered substrate included: 1.4 mM BCIP; 0.24 mM NBT; 100 mM Tris base (pH 9.6); and 50 mM MgCl$_2$. Various concentrations of Tris in solutions at several pH values were compared. The results are presented in Table 1 in which a 100 mM Tris buffer solution contained 50 mM MgCl$_2$, 1.4 mM BCIP and 0.24 mM NBT, and in which a 1.0 M Tris buffer solution contained 1.4 mM BCIP and 0.24 mM NBT.

TABLE 1

| pH | ΔA$_{575}$/min 0.1 M Tris | 1.0 M Tris |
|---|---|---|
| 9.0 | 0.071 | 0.151 |
| 9.2 | 0.115 | 0.174 |
| 9.4 | 0.126 | 0.224 |
| 9.6 | 0.180 | 0.261 |
| 9.8 | 0.118 | 0.252 |

TABLE 1-continued

| pH | ΔA$_{575}$/min 0.1 M Tris | 1.0 M Tris |
|---|---|---|
| 10.0 | ND | 0.222 |

As shown in Table 1, it was determined that a 1.0 M Tris solution at pH 9.6 was superior in performance to the original formulation. However, at pH 9.6, Tris (pK$_a$ =8.05) is well outside of its effective buffering range. Thus, no solutions of Tris were found to be useful within the range of pH values within which Tris is an effective buffer.

EXAMPLE 3

In an attempt to prevent the formation of the precipitate noted in the solutions of Example 2, organic solvents were added to the Tris-buffered substrate. The addition of as little as 50 mM ethanol, 50 mM dimethyl formamide or 50 mM dimethyl sulfoxide enhanced the formation of precipitate rather than inhibiting it. These results indicate that the addition of BCIP and NBT as a concentrate in organic solvents does not solve the precipitation problem.

EXAMPLE 4

In an attempt to provide an alternative to Tris which would increase the stability of the substrate formulation, several buffers were investigated.

All buffers were tested at 100 mM concentration, were adjusted to pH 9.5 and included 1 mM MgCl$_2$. The buffers were incubated at 45° C. In each substrate buffer the concentration of BCIP was 1.4 mM and the concentration of NBT was 0.24 mM. In parallel with a stability test of each buffer, the efficacy of each stored solution was tested in an HCG assay.

In a solid phase assay, a plurality of substantially spherical solid particles, having an average diameter of from about 0.1 to about 5 microns, were immobilized on a porous matrix of fibrous material. The fibrous material may be formed from glass, polystyrene-coated glass, cellulose, nylon or other fibrous materials known to interact with particles and to immobilize them. The particles may be composed of polystyrene, polymethacrylate, polypropylene, latex, polyacrylonitrile, polycarbonate or similar materials which have a surface capable of holding a substance to be analyzed.

For a human chorionic gonadotropin (HCG) assay, microparticles were prepared by adding 100 μl of carboxylate-modified polystyrene microparticles (commerically available from Seragen, Indianapolis, Ind.) to 1.0 ml of 5 mM methyl ethyl sulfonate (MES) buffer (pH 4.75) and 75 μl of anti-HCG antibody solution (2 mg/ml). The solution was stirred before adding 100 ml of 1-ethyl-3(3-dimethylaminopropyl) carbodimide HCl (EDAC) at a concentration of 0.5 mg/ml H$_2$O. The solution was stirred overnight at 2-8° C., after which the microparticles were isolated by centrifugation, washed twice with 0.1% Tween-20 centrifugation, washed twice with 0.1% Tween-20 solution, and resuspended in phosphate buffered saline (0.01 M KH$_2$PO$_4$ and 0.15 M NaCl at pH 7.2) to yield a 0.125% solution. After resuspension in phosphate buffered saline (PBS), the particles were stored at 2-8° for subsequent use.

Fifty μl of the antibody-coated microparticles were added dropwise to the center of a Whatman GF/D glass filter; 100 μl of pig sera were then added and the filter and the microparticles were incubated for 30 minutes in a humidity chamber at room temperature. After this time, the filter was washed three times in 300 μl of PBS buffer. The filter was then stored in a humidity chamber until used. That the microparticles were irreversibly trapped or agglomerated on the glass fibers of the filter material was confirmed by scanning electron microscopy.

Antibody-enzyme conjugates were prepared according to the procedure of Kearney et al., *Immunology*, 123, 1548 (1979) from mouse anti-HCG monoclonal antibodies. Alkaline phosphatase was obtained from Boehringer Mannheim GmbH, Indianapolis, Ind.

The glass filter material, containing antibody-coated microparticles was cut into substantially circular "disks" 12 mm in diameter, and the disks were placed in contact with a blotter material in order to absorb excess fluid. Thereafter, five drops (about 280μl) of standard samples of human urine (commercially available from Scripps Institute, San Diego, Calif.) containing zero, or 50 or 100 mIU/ml levels of HCG were added to matrix through a prefilter situated above each matrix. Three drops of the antibody-enzyme conjugate were then added to each matrix through the prefilter, and each matrix was incubated at room temperature for about two minutes. The prefilter was next removed, and 1.0 ml of a detergent wash solution (including citrate, phosphate and and Tween 20) was added to each matrix to remove any excess antibody-enzyme conjugate. The matrix was again placed on a blotter and 5 drops (about 250μl) of substrate buffer to be tested were added to each matrix. After two minutes, 1 ml of the wash solution was added and each matrix checked visually for color development. Color development was observed for the test samples which contained HCG, and the absorbance corresponding to the color development was determined instrumentally using a conventional spectrophotometer. The results are presented in Table 2 in which the number of days of incubation at 45° C. and the reason for rejection are indicated.

TABLE 2

| Buffer | Testing Period (In days at 45° C.) | Reason for Rejection |
|---|---|---|
| Sodium Borate | 3 | No color development after 3 days at 45° C. |
| Sodium Carbonate | 3, 4, 6, 20 | Poor color development after 20 days at 45° C. |
| Triethanolamine | 3, 4, 6, 20 | Particle development by 20 days at 45° C. |
| Ethanolamine | 3, 4, 6, 20 | Particle development by 20 days at 45° C. |
| Glycine | 3 | Particle development by 20 days at 45° C. |
| Tris (hydroxyethyl) Amino Methane | 3, 4, 6, 20 | Particle development by 20 days at 45° C. |
| Phenol | 0 | Insoluble precipitates immediately formed |
| CHES (2-[N—cyclohexylamino] Ethane Sulfonic Acid) | 0 | Insoluble precipitates immediately formed |
| Piperazine | 4 | Particles developed within 4 days at 45° C. |
| Alanine | 4 | Particles developed within 4 days at 45° C. |
| 2-Amino-2-Methyl-1, 3-Propandiol | 4 | Particles developed within 4 days at 45° C. |

As indicated in Table 2, each of these buffers proved to be unsatisfactory, either by inhibiting the enzyme or by enhancing precipitation of the chromogen. In phenol and CHES, NBT was insoluble even prior to incubation (i.e., at "0" days).

In test tube assays as described in Example 2, Tris buffer solutions at pH 9.6 and at 0.1M and 1.0 M were compared with 1.0 M diethanolamine (pH 9.3) and 0.1 M 2A2M1P (pH 9.8) in a 11.4 mM BCIP and 0.24 mM NBT substrate formulation. The results are presented in Table 3.

TABLE 3

| Buffer | Comments |
|---|---|
| 0.1 M Tris (pH 9.6) | Rate of color formation slow ($\Delta A_{575}$/min = 0.17). Precipitate formed after several (approx. 7) days at room temperature or within 24 hrs. at 45° C. |
| 1.0 M Tris (pH 9.6) | Rate of color formation good ($\Delta A_{575}$/min = 0.30). Precipitate formed after several days (approx. 3) days at room temperature. |
| 0.1 M Diethanolamine (pH 9.3) | Rate of color formation very good ($\Delta A_{575}$/min = 0.34). Precipitate formed within 24 hrs. at room temperature. |
| 0.1 M 2A2M1P (pH 9.8) | Rate of color formation good ($\Delta A_{575}$/min = 0.30). Stable at room temperature for at least 2 months. Stable at 45° C. for 7 days. |

In Table 2, 1 0 M Tris and 1.0 M diethanolamine were not tested at 45° C. due to the appearance of a precipitate at room temperature within a few days.

Thus, substrates prepared in 1.0 M Tris were observed to precipitate much more readily than those prepared in 0.1 M Tris. More importantly, in these experiments 2AM1P was the only buffer which exhibited a combination of efficacy and useful shelf life in the presence of a substrate formulation (chromogen).

EXAMPLE 5

In another series of experiments, the rate of color formation in substrates prepared in 2A2M1P was compared to the rate of color formulation of the same substrates in Tris. For each assay, 20μl of conjugate (as in Example 2) were mixed with 1.0 ml of substrate formulation and color development was monitored spectrophotometrically. The solutions were: 0.1 M 2A2M1P (pH 9.8), 1.4 mM BCIP, 0.24 mM NBT and 1.0 mM MgCl$_2$; and 0.1 M Tris (9.6), 1.4 mM BCIP, 0.24 mM NBT and 50 mM MgCl$_2$.

In a plot of optical density (O.D.) at 575 nm versus time, as illustrated in FIG. 1, in which the results for 2A2M1P are graphed as curve A and the results for Tris are graphed as curve B, the rate of color development is shown to be roughly linear after 2 minutes.

Employing Equation (1), for 0.1 M 2A2M1P, $$\Delta A/\min = \frac{(0.683 - 0.298)}{2} = 0.192 \quad (2)$$

For 0.1 M Tris, $$\Delta A/\min = \frac{(0.548 - 0.241)}{2} = 0.154 \quad (3)$$

EXAMPLE 6

Experiments were performed to determine the concentration of BCIP and NBT which would give a strong signal of an acceptable color and enhanced stability in 2A2M1P.

To determine the concentrations of BCIP and NBT which meet these requirements, a matrix of nine substrates was prepared in 0.1 M 2A2M1P (pH 9.8) containing 1.0 mM $MgCl_2$. BCIP concentrations were 2.3 mM, 1.4 mM, or 1.0 mM. NBT concentrations were 0.24 mM, 0.10 mM, or 0.05 mM. These substrates were assayed both in a test tube assay, according to Example 2, and on assays for Group A Streptococcus. The results of the test tube assay are presented in Table 4 as $\Delta A_{575}$/min.

TABLE 4

|  |  | NBT | | |
|---|---|---|---|---|
|  |  | 0.25 mM | 0.10 mM | 0.05 mM |
|  | 2.3 mM | 0.292 | 0.284 | 0.184 |
| BCIP | 1.3 mM | 0.301 | 0.285 | 0.212 |
|  | 1.0 mM | 0.264 | 0.245 | 0.191 |

For Table 4, a reference substrate buffer formulation (containing 0.1 M Tris (9.6), 50 mM $MgCl_2$, 1.4 mM BCIP and 0.24 mM NBT) exhibited an $\Delta A_{575}$/min of 0.174.

In a Group A Streptococcus assay, the results of which appear in Table 5, 3 drops of a solution of streptococcal extract (from $5 \times 10^4$ cells per ml) were added to a matrix to which rabbit anti-Group A Streptococcus antibody-coated, polystyrene microparticles had been bound. Next, 3 drops of a solution of alkaline phosphatase-conjugated, rabbit anti-Group A Streptococcus antibody were added. The matrix was washed, substrate formulation was added and color was developed for 2 min. The matrix was then washed prior to measuring color intensity with a reflectance reader. The results are presented in Table 5 in which a lower reflectance indicates a darker spot and for which a reference buffer formulation [0.1 M Tris (pH 9.6); 50 mM $MgCl_2$; 1.4 mM BCIP; and 0.24 mM NBT] exhibited a reflectance of 37.0 in the assay.

TABLE 5

|  |  | 0.25 mM | 0.10 mM | 0.05 mM |
|---|---|---|---|---|
| BCIP |  | Dark Purple | Dark Blue | Dark Blue |
|  | 2.3 mM | 37.5 | 36.5 | 39.1 |
|  |  | Dark Purple | Blue/Purple | Dark Blue |
|  | 1.3 mM | 39.3 | 33.6 | 37.8 |
|  |  | Purple | Blue | Blue |
|  | 1.0 mM | 42.0 | 38.4 | 46.6 |

As indicated in Table 5, reducing NBT to 0.05 mM shifted the color of the precipitate on the matrix from purple to blue. While the reflectance reader detected little difference, the blue color was not visually perceived as being as dark as a purple spot with comparable reflectance. Three substrate formulations were consistently selected as having superior performance both in visual perception of color and optical reflectance measurements. These were: 1.4 mM BCIP, 0.24 mM NBT; 1.4 mM BCIP, 0.10 mM NBT; and 1.0 mM BCIP, 0.24 mM NBT.

EXAMPLE 7

Substrate preparations were incubated at 45° C. to provide a short-term indication of long-term stability at room temperature.

An HCG assay, as described in Example 4, was conducted for each substrate prepared in 0.1 M 2A2M1P (pH 9.8), 1.0 mM $MgCl_2$ pH 9.8 and stored at 45° C. in the dark in glass vials.

Table 6 shows the day that a visible precipitate appeared in the substrates from the BCIP/NBT matrix after storage at 45° C.

TABLE 6

Formation of Precipitate at 45° C. in Substrate with Variations in Chromogen Concentration

|  |  | NBT | | |
|---|---|---|---|---|
|  |  | 0.25 mM | 0.10 mM | 0.05 mM |
| BCIP | 2.3 mM | 4 days | 4 days | 7 days |
|  | 1.3 mM | 7 days | 7 days | 10 days |
|  | 1.0 mM | 10 days | 10 days | 10 days |

As indicated in Table 6, substrates containing 1.4 mM BCIP and 0.24 mM NBT in 0.1 M Tris, 0.1 M 2A2M1P, and 0.1 M 2A2M1P remained stable for 4 days. When $MgCl_2$ was added to these same solutions, no precipitate was detected until day 12. These studies indicate that the formation of precipitate can be retarded by decreasing the concentration of BCIP and NBT in combination with the addition of $MgCl_2$.

EXAMPLE 8

Optimum conditions for using 2A2M1P ($pK_a$ 9.3) as a buffer were explored.

Figure 2:
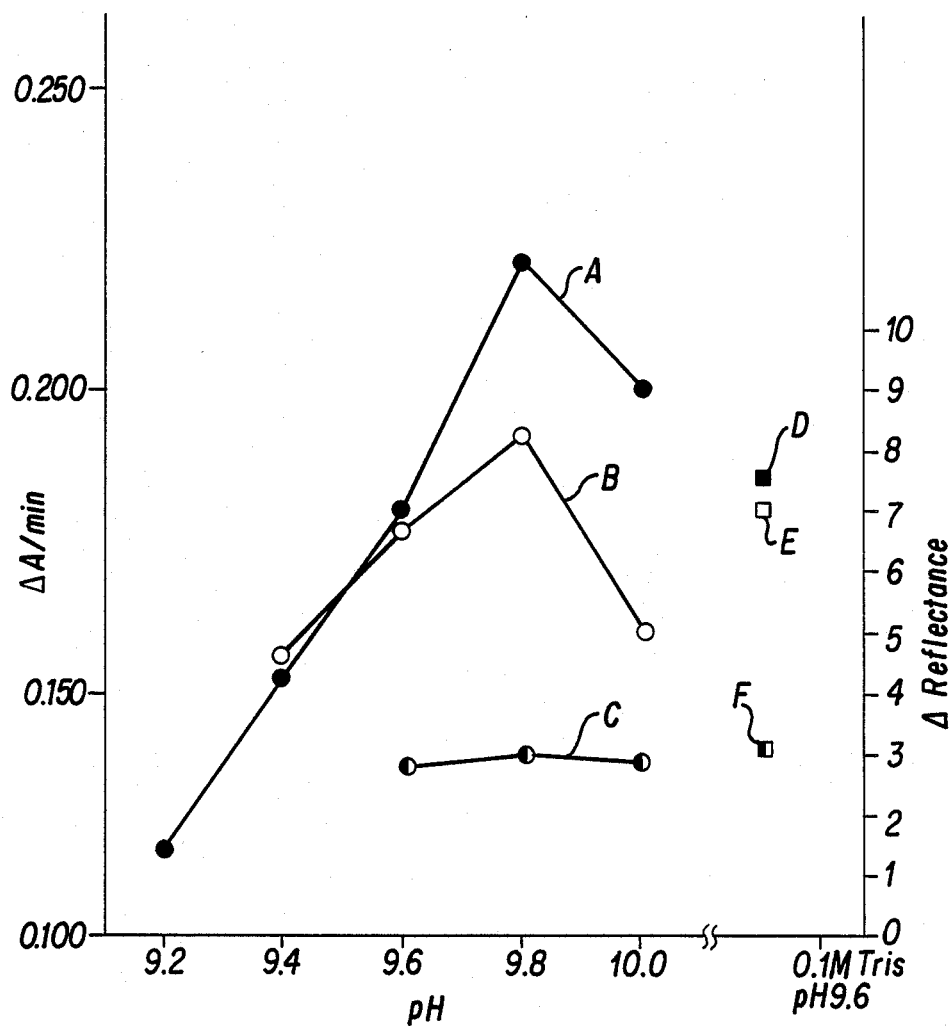
FIG. 2 is a graphic depiction of the results of assays performed in 2A2M1P buffer at several values of pH.

As illustrated in FIG. 2, an optimum pH was determined for substrate prepared in 2A2M1P. Substrates were assayed in a tube assay (curve A), according to Example 2, and in a Rubella virus assay with high positive serum containing a high level of antibody to Rubella (curve B) and negative (curve C) samples. Substrate prepared in 0.1 M Tris pH 9.6 was included as a control for D in a tube assay, for E in a Rubella high positive assay as in B; and for F in an assay negative for Rubella negative.

Each formulation contained 1.4 mM BCIP, 0.24 mM NBT, and 1.0 mM $MgCl_2$ in 100 mM 2A2M1P. The pH of each solution was adjusted using concentrated HCl. Microparticles were coated with Rubella virus, followed by exposure to human serum containing antibodies against Rubella virus and then alkaline phosphatase-conjugated rabbit anti-human antibodies.

Curve A is an indication of the rate of color formation in a test tube assay of substrate buffered in 2A2M1P at differing pH. By comparison, point D is an indication of the rate of color formation of substrate buffered in Tris (0.1 M pH 9.6 containing 50 mM $MgCl_2$).

Each of the substrate preparations were analyzed using the Rubella assay. Serum with high levels of antibody to Rubella (high positive) or negative for antibody to Rubella were passed through the matrix. This was followed by anti-human, alkaline phosphatase conjugated antibody as in Example 4. After suitable washing, substrate was added and color developed for 2 minutes. Color development was stopped by washing to remove excess substrate and color intensity measured on a reflectance reader. Curve B shows the signal generated by a high positive sample and curve C shows the signal generated by a negative sample. Points E and F indicate the reflectance of spots formed using substrates buffered in 0.1 M Tris, 50 mM MgCl$_2$ pH 9.6 (1.4 mM BCIP, 0.24 mM NBT).

As indicated in FIG. 2, the pH optimum for substrate buffered with 2A2M1P was 9.8 in a 0.1 M solution both in the test tube assay and in the Rubella assay. No additional signal was observed when the 2A2M1P concentration was increased to 1.0 M.

The components of the substrate formulation according to the present invention have been tested in a test tube assay according to Example 2 (1.0 ml substrate/20 μl of conjugate) at different concentrations of BCIP and NBT.

Table 7 includes results for various concentrations of BCIP in 0.1 M 2A2M1P (pH 9.8), 1.0 mM MgCl$_2$ and 0.24 mM NBT.

TABLE 7

| Concentration of BCIP | $\Delta A_{575}$/min |
|---|---|
| 1.0 mM | 0.192 |
| 2.5 mM | 0.244 |
| 5.0 mM | 0.209 |
| 10.0 mM | 0.098 |

Table 8 presents results for several concentrations of NBT in 0.1 M 2A2M1P (pH 9.8), 1.0 mM MgCl$_2$, and 2.3 mM BCIP.

TABLE 8

| Concentration of BCIP | $\Delta A_{575}$/min |
|---|---|
| 0.05 mM | 0.267 |
| 0.10 mM | 0.360 |
| 0.25 mM | 0.382 |
| 0.50 mM | 0.340 |

As indicated in Table 7, it was found that concentrations of BCIP between 1.0 mM and 10 mM work well. Concentrations of NBT between 0.05 and 0.5 mM were also found to work well as shown in Table 8. Although 2A2M1P has only been employed in these examples at 0.1 M and 1.0 M, the buffer may work well at other concentrations.

An investigation of the optimal pH range of 2A2M1P under the conditions given for Table 1 above and in parallel with the experiments reported therein produced the results given in Table 9.

TABLE 9

| pH | $\Delta A_{575}$/min<br>0.1 M 2A2M1P |
|---|---|
| 9.0 | ND |
| 9.2 | 0.114 |
| 9.4 | 0.152 |
| 9.6 | 0.180 |
| 9.8 | 0.221 |
| 10.0 | 0.200 |

Based upon the results reported in Table 9, 2A2M1P substrate formulations according to the present invention are preferably adjusted to within a pH range from 9.7 to 9.9.

The role of magnesium in substrate solutions is not settled. Magnesium salts have very low solubilities at high pH, approximately 1.4 mM at pH 10.3. The addition of trace amounts of magnesium (10 to 1000 μM) had no effect on the signal generated by these substrates. However, the addition of 1 mM MgCl$_2$ suppresses chromogen precipitation when the substrate is stressed at 45° C.

An important concern in the formulation is the stability of the substrate. While the change to 2A2M1P enhances the stability, the temperature stress studies reported in Example 7 indicate that decreasing the concentrations of BCIP and NBT will also increase stability. Therefore, it is currently preferred that concentrations of 1.2 mM BCIP and 0.17 mM NBT be employed in substrate formulations according to the present invention.

On the basis of the above results, a preferred alkaline phosphatase substrate formulation according to the present invention includes: 100 mM 2A2M1P (pH 9.8); 1.2 mM BCIP; 0.17 mM NBT; 1.0 mM MgCl$_2$; and 0.02% sodium azide. For one liter of solution, 140 mg NBT is mixed with approximately 475 ml of distilled water and stirred in the dark for 30 min to prepare a Solution A. Next, to prepare a Solution B, 10 ml of 2A2M1P is added to 450 ml of distilled H$_2$O while stirring and the solution is mixed for at least 5 min. To Solution B 520 mg of BCIP are added and stirring is continued under reduced light for at least 20 min. The pH of Solution B is adjusted to 9.8 (range 9.7 to 9.9) with 6.0 N HCl. Solutions A and B are mixed slowly while stirring. One ml of an aqueous solution of 1.0 M MgCl$_2$ is added to the mixture, followed by addition of 200 mg of sodium azide. The solution is stirred until all solids are dissolved. The volume is made up to 1.0 liter with H$_2$O. The solution is then filtered through 0.2 micrometer Nalgene filter and stored at 2°–8° C. in the dark. In preparing this substrate, the NBT should be dissolved in distilled water prior to the addition of 2A2M1P to avoid problems with insolubility in 0.1 M 2A2M1P.

EXAMPLE 9

The stability of the reformulated alkaline phosphatase substrate solution of Example 8 was tested. The substrate solution was stored at ambient temperature, at 2°–8° C., at 37° C., and at 45° C. After the number of days of storage indicated in Table 10, samples were assayed in the HCG assay of Example 4.

TABLE 10

| | | | % Correct Diagnosis of Standards | | | |
|---|---|---|---|---|---|---|
| | | | HCG (mIU/ml) | | | |
| Day | Temp | Reps | 0 | 50 | 250 | Comments |
| 7 | 2–8 | 3 | 100 | 100 | 100 | No problems. |
| 7 | Amb | 3 | 100 | 100 | 100 | |
| 7 | 37 | 3 | 100 | 100 | 100 | |
| 7 | 45 | 3 | 100 | 100 | 100 | |
| 13 | 2–8 | 3 | 100 | 100 | 100 | No problems. |
| 13 | Amb | 3 | 100 | 100 | 100 | |
| 13 | 37 | 3 | 100 | 100 | 100 | |
| 13 | 45 | 3 | 100 | 100 | 100 | |
| 19 | 2–8 | 3 | 100 | 100 | 100 | Some specks on |
| 19 | Amb | 3 | 100 | 100 | 100 | matrix at 37 and |
| 19 | 37 | 3 | 100 | 100 | 100 | 45. Some specks |
| 19 | 45 | 3 | 100 | 100 | 100 | in 45 degree bottle. |
| 21 | 2–8 | 3 | 100 | 100 | 100 | 37 and 45 were a bit |
| 21 | Amb | 3 | 100 | 100 | 100 | lighter than other |
| 21 | 37 | 3 | 100 | 100 | 100 | 2 and had a few |
| 21 | 45 | 3 | 100 | 100 | 100 | speckles. |
| 28 | 2–8 | 3 | 100 | 100 | 100 | 37 and 45 showed |
| 28 | Amb | 3 | 100 | 100 | 100 | reduced signal and |
| 28 | 37 | 3 | 100 | 100 | 100 | speckles. |
| 28 | 45 | 3 | 100 | 0 | 100 | |
| 35 | 2–8 | 3 | 100 | 0 | 100 | Same as for 28 above |
| 35 | Amb | 3 | 100 | 0 | 100 | with higher |
| 35 | 37 | 3 | 100 | 0 | 100 | temperatures |
| 35 | 45 | 3 | 100 | 0 | 100 | showing more precipitate on matrices and in |

TABLE 10-continued

| | | | % Correct Diagnosis of Standards | | | |
|---|---|---|---|---|---|---|
| | | | HCG (mIU/ml) | | | |
| Day | Temp | Reps | 0 | 50 | 250 | Comments |
| | | | | | | bottles. |
| 47 | 2-8 | 3 | 100 | 0 | 100 | Same as above. |
| 47 | Amb | 3 | 100 | 0 | 100 | |
| 47 | 37 | 3 | 100 | 0 | 100 | |
| 47 | 45 | 3 | 100 | 0 | 100 | |
| 72 | 2-8 | 3 | 100 | 33 | 100 | Same as above. |
| 72 | Amb | 3 | 100 | 33 | 100 | |
| 72 | 37 | 3 | 100 | 0 | 100 | |
| 72 | 45 | 3 | 100 | 0 | 100 | |
| 77 | 2-8 | 3 | 100 | 100 | 100 | 45 and 37 matrices |
| 77 | Amb | 3 | 100 | 100 | 100 | have a "dirty |
| 77 | 37 | 3 | 100 | 100 | 100 | laundry" |
| 77 | 45 | 3 | 100 | 100 | 100 | appearance but are very efficacious. |
| 90 | 2-8 | 3 | 100 | 100 | 100 | Same as above. |
| 90 | Amb | 3 | 100 | 100 | 100 | |
| 90 | 37 | 3 | 100 | 100 | 100 | |
| 90 | 45 | 3 | 100 | 100 | 100 | |
| 98 | 2-8 | 3 | 100 | 100 | 100 | Same as above. |
| 98 | Amb | 3 | 100 | 100 | 100 | |
| 98 | 37 | 3 | 100 | 100 | 100 | |
| 98 | 45 | 3 | 100 | 100 | 100 | |
| 107 | 2-8 | 3 | 100 | 100 | 100 | Same as above. |
| 107 | Amb | 3 | 100 | 100 | 100 | |
| 107 | 37 | 3 | 100 | 100 | 100 | |
| 107 | 45 | 3 | 100 | 100 | 100 | |
| 111 | 2-8 | 3 | 100 | 100 | 100 | 37 and 45 have a |
| 111 | Amb | 3 | 100 | 100 | 100 | light haze. 2-8 |
| 111 | 37 | 3 | 100 | 100 | 100 | and ambient looked |
| 111 | 45 | 3 | 100 | 100 | 100 | excellent. |

EXAMPLE 10

Figure 3:
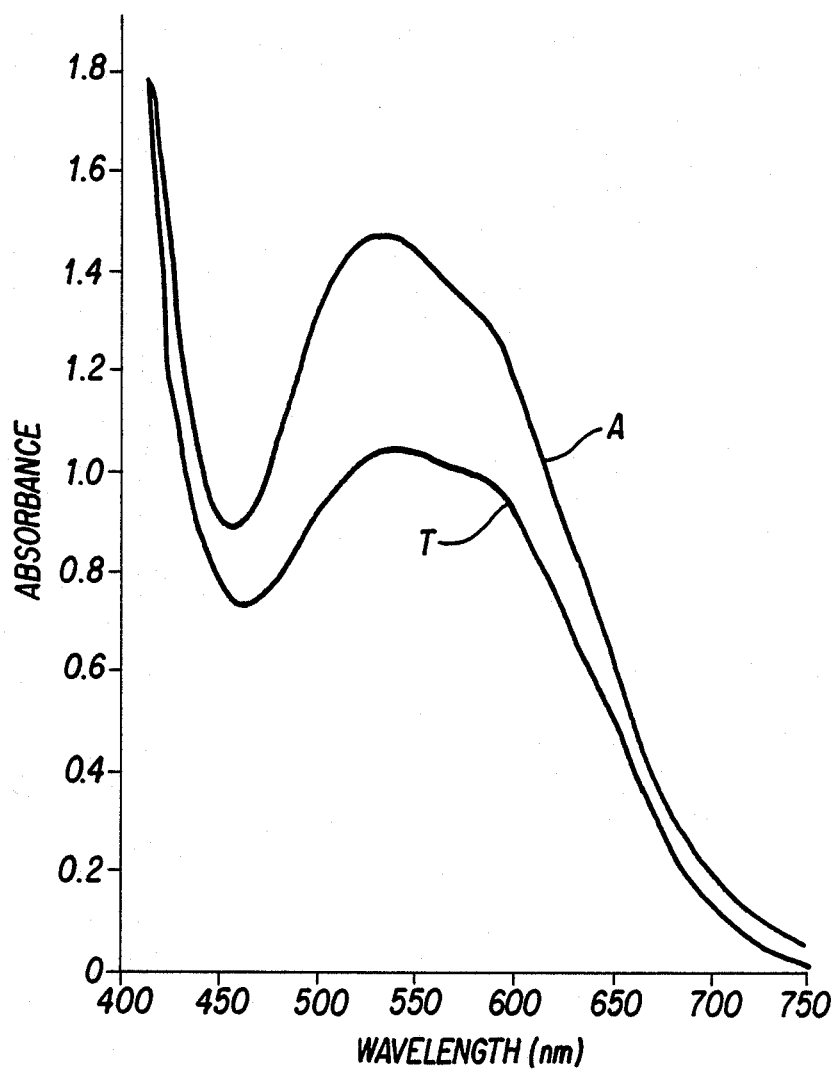
FIG. 3 is a graphic depiction of absorption spectra of products formed by the reaction of substrates with alkaline phosphatase either in 2A2M1P buffer or in Tris buffer.

A spectrophotometric comparison of the product of the 2A2M1P-buffered substrate according to the present invention with the product of a Tris-buffered substrate is found in FIG. 3.

In FIG. 3, the absorption spectra of products formed by the reaction of substrates with alkaline phosphatase are presented. Line A represents results for a substrate prepared in 0.1 M aqueous solution of 2A2M1P (pH 9.6) and 1.0 mM MgCl$_2$ containing 1.2 mM BCIP and 0.17 mM NBT. Line T represents results for a substrate prepared in 0.1 M Tris (pH 9.6) and 50 mM MgCl$_2$ containing 1.4 mM BCIP and 0.24 mM NBT.

As indicated by the results presented in FIG. 3, the products of both formulations are essentially the same.

EXAMPLE 11

The present invention may be employed in a solid phase assay. An example of a solid phase assay is an assay for HCG of the sort described in Example 4 but with an unknown in place of a standard urine sample. In such an assay particles are coated with antibody specific for HCG and are trapped in a glass fiber matrix. A urine sample from a patient is passed through the matrix. If HCG is present in the urine, HCG binds to the HCG-specific antibody.

A second antibody specific for HCG is conjugated to alkaline phosphatase. By passing a solution of the second antibody through the matrix, the second antibody binds to any HCG therein.

After washing and incubation of the matrix with the substrate formulation according to the present invention, any reaction is stopped by washing excess substrate from the matrix.

In the presence of HCG, alkaline phosphatase-conjugated antibody bound to the HCG reacts with the substrate formulation to produce a dark, blue-black spot. In the absence of HCG, the conjugated antibody is washed away and no spot is formed.

EXAMPLE 12

The substrate formulation according to the present invention may be employed in an enzyme-linked immunosorbent assay for the purpose of determining the presence of an antibody in a blood sample. In such an assay, a specific antigen is spotted on nitrocellulose. The nitrocellulose is incubated with a patient sample followed by incubation with an alkaline phosphate-conjugated antibody against human antibody. Subsequent incubation of the nitrocellulose with the substrate formulation according to the present invention results in the formation of a blue-black colored spot if an antibody specific for the spotted antigen is present in the sample. If no such antibody is present, no spot forms.

EXAMPLE 13

The substrate formulation according to the present invention may be employed in a Western Blot assay. In this sort of assay, proteins are transferred from electrophoretic gels to nitrocellulose. The nitrocellulose may be probed for a specific protein by incubation with an alkaline phosphatase-conjugated antibody against the specific protein, followed by incubation with the substrate formulation according to the present invention. If the protein is present, the conjugated antibody binds to it and reaction products of the alkaline phosphatase and the substrates are deposited at the location of the protein.

The buffered phosphatase substrate according to the present invention achieves two goals: first, to provide additional stability and second, to enhance the signal or signal-to-noise ratio. An enhancement of signal-to-noise ratio for 2A2M1P over Tris is demonstrated by a higher signal in the test tube assay of Example 5 and in the stronger color in the Rubella assay of Example 8.

The change from Tris to 2A2M1P with trace amounts of Mg++ has increased the stability of the preparation. In addition, substrate prepared in 2A2M1P had a greater ΔA/min in a test tube assay and at least comparable signals in the assays to Tris buffered substrates.

Although the present invention is described in terms of a preferred embodiment, it is understood that modifications and improvements will occur to those skilled in the art. For example, although BCIP has been employed in the preferred embodiment, it is expected that other indigo cogeners may be employed in the present invention, including indolyl phosphate if an appropriate oxidant, such as K$_3$Fe(CN)$_6$ is supplied. It is also expected that other tetrazolium salts may be employed in the present invention and, in fact, tetra nitro blue tetrazolium was observed to form a colored spot useful as an indicator in the HCG assay of Example 4. Accordingly it is intended that the appended claims include all such equivalent variations which come within the scope of the invention as claimed.

What is claimed is:

1. A substrate formulation for an alkaline phosphatase assay comprising:
   a phosphated indigo cogener;
   a tetrazolium salt at a concentration effective to produce a detectable signal upon reaction with said phosphated indigo cogener; and 2-amino-2-methyl-1-propanol at a concentration effective to buffer a reaction between said phosphated indigo cogener and said tetrazolium salt in aqueous solution within a range of pH which allows the reaction to proceed.

2. The substrate formulation as recited in claim 1 wherein said phosphated indigo cogener is 5bromo-4-chloro-3-indolyl phosphate.

3. The substrate formulation as recited in claim 2 wherein said 5-bromo-4-chloro-3-indolyl phosphate is at a concentration between about 1.0 mM and about 10 mM.

4. The substrate formulation as recited in claim 1 wherein said tetrazolium salt is nitro blue tetrazolium.

5. The substrate formulation as recited in claim 4 wherein said nitro blue tetrazolium is at a concentration between about 0.05 mM and about 0.5 mM.

6. The substrate formulation as recited in claim 1 wherein said 2-amino-2-methyl-1-propanol is at a concentration between about 0.1M and about 1.0 M.

7. A substrate formulation in aqueous solution for an alkaline phosphatase assay comprising:
 5-bromo-4-chloro-3-indolyl phosphate at a concentration between about 1.0 mM and about 10 mM.;
 nitro blue tetrazolium at a concentration between about 0.05 mM and about 0.5 mM; and
 2-amino-2-methyl-1-propanol at a concentration between about 0.M and about 1.0 M.

8. The substrate formulation as recited in claim 7, further comprising $MgCl_2$ at a concentration of about 1.0 mM.

9. The substrate formulation as recited in claim 8 wherein:
 said 5-bromo-4-chloro-3-indolyl phosphate is at a concentration of 1.2 mM;
 said nitro blue tetrazolium is at a concentration of 0.17 mM; and
 said 2-amino-2-methyl-1-propanol is at a concentration of 100 mM.

10. The substrate formulation as recited in claim 9, further comprising sodium azide at a concentration of 0.02%.

* * * * *

UNITED STATES PATENT AND TRADEMARK OFFICE
CERTIFICATE OF CORRECTION

PATENT NO. : 4,748,115
DATED : May 31, 1988
INVENTOR(S) : Jeffrey W. Steaffens

It is certified that error appears in the above—identified patent and that said Letters Patent is hereby corrected as shown below:

Column 13, line 8: Change --5bromo-4- -- to "5-bromo-4-"

Column 14, line 8: Change --0.M-- to "0.1M"

Signed and Sealed this

Eleventh Day of October, 1988

Attest:

DONALD J. QUIGG

Attesting Officer

Commissioner of Patents and Trademarks